United States Patent
Arai et al.

(10) Patent No.: US 7,331,924 B2
(45) Date of Patent: Feb. 19, 2008

(54) ENDOSCOPE APPARATUS HAVING ELECTRIC BENDING ENDOSCOPE

(75) Inventors: Keiichi Arai, Hachioji (JP); Takemitsu Honda, Hino (JP); Seiichiro Kimoto, Hachioji (JP); Takayasu Miyagi, Hachioji (JP); Toshinari Maeda, Hachioji (JP); Yuichi Ikeda, Tama (JP); Toshimasa Kawai, Yokohama (JP)

(73) Assignee: Olympus Corporation, Tokyo (JP)

( * ) Notice: Subject to any disclaimer, the term of this patent is extended or adjusted under 35 U.S.C. 154(b) by 92 days.

(21) Appl. No.: 10/393,722

(22) Filed: Mar. 21, 2003

(65) Prior Publication Data

US 2004/0034279 A1 Feb. 19, 2004

(30) Foreign Application Priority Data

Mar. 22, 2002 (JP) ............................. 2002-081552

(51) Int. Cl.
*A61B 1/00* (2006.01)
(52) U.S. Cl. ........................................................ 600/145
(58) Field of Classification Search ........ 600/117–118, 600/145–146, 148–150, 103
See application file for complete search history.

(56) References Cited

U.S. PATENT DOCUMENTS

| 4,483,326 | A | * | 11/1984 | Yamaka et al. | ............. | 600/149 |
| 4,700,693 | A | * | 10/1987 | Lia et al. | ..................... | 600/141 |
| 4,895,431 | A | * | 1/1990 | Tsujiuchi et al. | ............. | 359/29 |

(Continued)

FOREIGN PATENT DOCUMENTS

JP 6-269398 9/1994

Primary Examiner—John P. Leubecker
Assistant Examiner—Philip R Smith
(74) Attorney, Agent, or Firm—Scully, Scott, Murphy & Presser, P.C.

(57) ABSTRACT

An electric bending endoscope apparatus includes an electric bending endoscope, a bending control device for controlling a bending direction and the amount of bending of a bending portion based on a bending instructing signal outputted from a portion for instructing a bending operation in the electric bending endoscope, an image processing device for generating an observing image captured by the electric bending endoscope to a video signal, and a display device for displaying the video signal generated by the image processing device as an endoscope image, wherein the electric bending endoscope includes a bending driving portion for bending the bending portion arranged at an inserting portion, a bending motive portion for driving the bending driving portion, a portion for restoring transmission and disconnection of driving force that reversibly switches a status for transmitting the driving force by transmitting the driving force of the bending motive portion to the bending driving portion and a status for disconnecting the driving force, a portion for detecting a bending status which detects an operating status of the bending driving portion and detects the bending status of the bending portion, a portion for instructing a bending operation having a portion for inputting the bending instructing signal that outputs the bending instructing signal for relatively changing the bending direction and the amount of bending of the bending portion, a portion for detecting a predetermined bending status which detects that the bending portion is in at least one predetermined bending status, and a portion for notifying the predetermined bending status which sends a notification indicating that the bending portion is in the predetermined bending status based on a detecting result of the portion for detecting the predetermined bending status.

19 Claims, 11 Drawing Sheets

U.S. PATENT DOCUMENTS

| | | | |
|---|---|---|---|
| 4,982,725 A | * | 1/1991 | Hibino et al. ................ 600/117 |
| 5,469,840 A | * | 11/1995 | Tanii et al. .................. 600/117 |
| 5,520,222 A | * | 5/1996 | Chikama .................... 138/118 |
| 5,658,238 A | * | 8/1997 | Suzuki et al. ................ 600/150 |
| 6,236,876 B1 | * | 5/2001 | Gruner et al. .............. 600/407 |
| 6,320,284 B1 | * | 11/2001 | Fontana et al. ................ 310/12 |

* cited by examiner

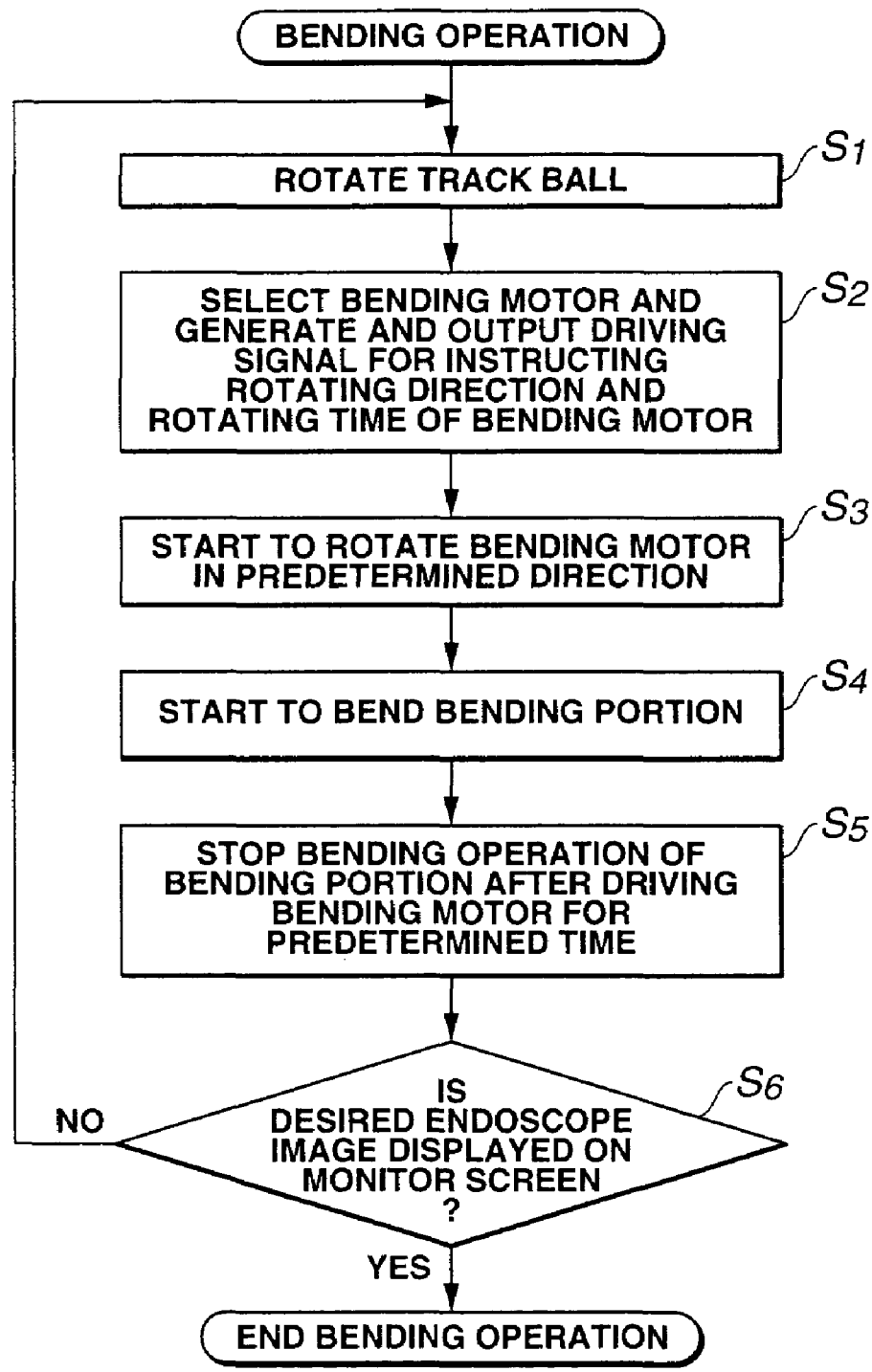

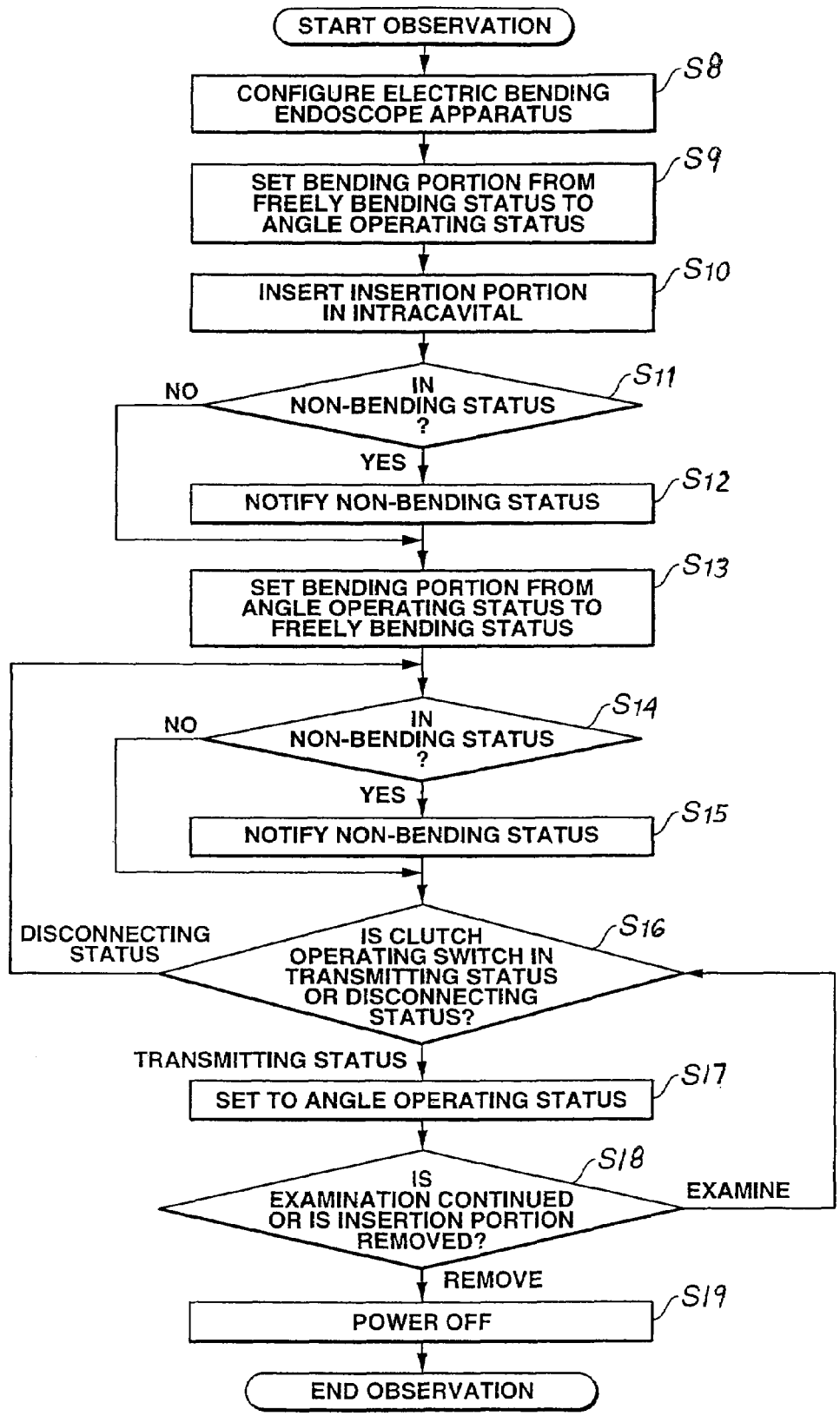

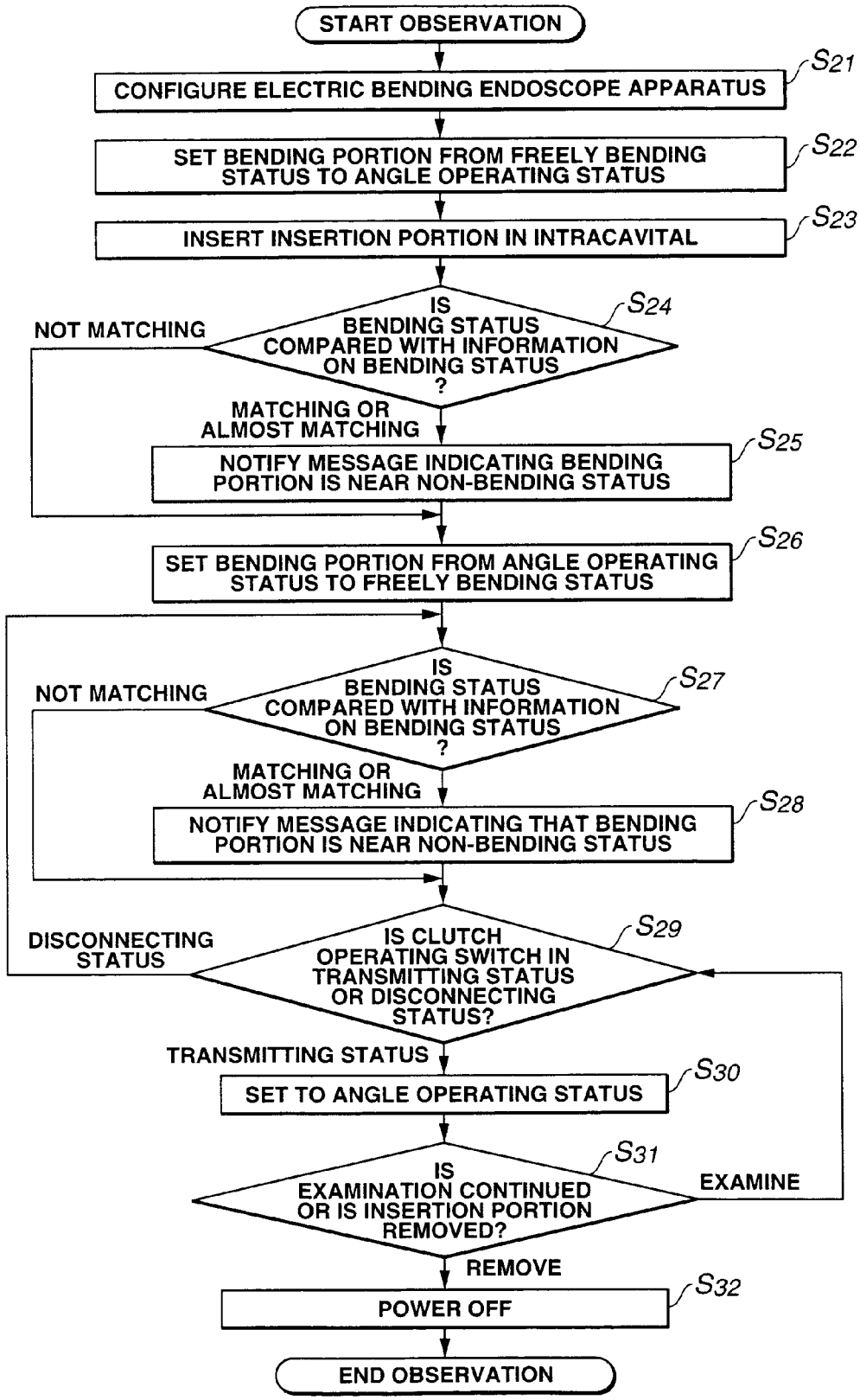

FIG.13A  FIG.13B

ENDOSCOPE APPARATUS HAVING ELECTRIC BENDING ENDOSCOPE

This application claims benefit of Japanese Application No. 2002-81552 filed on Mar. 22, 2002 the contents of which are incorporated by this reference.

BACKGROUND OF THE INVENTION

1. Field of the Invention

The present invention relates to an electric bending endoscope apparatus having an electric bending endoscope.

2. Description of the Related Art

Recently, an endoscope is widely used for various curing treatments which are performed by inserting an elongated inserting portion in the celom so as to observe the organ in the celom or by using a treatment tool inserted through a processing tool channel as needed.

The endoscope generally has a bending portion which is bent vertically or horizontally, or vertically and horizontally at a distal portion of the inserting portion. The bending portion is bent in a desired direction by stretching and contracting a bending wire which is inserted in the inserting portion.

In general, the bending wire is stretched or contracted by a bending knob manually. However, the endoscope recently includes an electric bending endoscope which is stretched by bending motive means such as an electric motor. In the electric bending endoscope, the bending portion is bent by operating, for example, bending operation instructing means such as a joystick arranged to an operating portion. In other words, the electric motor is rotated by a predetermined amount based on an operation instructing signal from the bending operation instructing means. Then, the rotation of the electric motor is transmitted to a pulley, the bending wire wound to the pulley is stretched, and the bending portion is bent. In the above-mentioned electric bending endoscope, the bending portion is easily and desirably bent by a single finger. Accordingly, the operability is improved because another finger operates another switch arranged to the operating portion.

However, in the electric bending endoscope, the bending wire is always under tension irrespective of in a bending status or non-bending status. Then, the following is requested to the electric bending endoscope.

(1) Since the bending wire is always under tension, the tension causes the stretch of the bending wire. In order to prevent the stretch of the bending wire, unnecessary tension should be prevented upon cleaning, storing, and carrying.

(2) When the tension is always placed, external force to the inserting portion during the inserting operation does not change the bending status of the bending portion. Thus, the tension is not placed to the bending wire and, in this status, a freely bending status is requested. In this status, the bending status of the bending portion freely changes in accordance with the external force acted on the inserting portion, namely, the bending portion is freely bent and changed.

(3) When a default is caused during the inserting operation or when a failure is caused in examination, it is requested that the freely bending status is obtained and the inserting portion is removed from the celom.

Endoscopes to respond to the above requests are proposed. For example, an electric bending endoscope has means for restoring transmission and disconnection of driving force which can switch a disconnecting status/connecting status of the tension acting on the bending wire in accordance with the necessity. Further, Japanese Unexamined Patent Application Publication No. 6-269398 discloses an endoscope which surely switches a locking status and a free status of the bending portion by arranging switching means which can switch a stretching status and a contracting status of a stretching member.

Furthermore, an electric bending endoscope includes the means for restoring the transmission and disconnection of the driving force and bending operation instructing means in which a track ball for instructing the bending operation of the bending portion as the change in relative position is arranged to the operating portion. In the electric bending endoscope having the track ball, the bending status of the bending portion is relatively changed in the operating direction by operating tracking ball, the stop of the operation of the track ball enables a re-operation waiting status, and the stop point becomes a re-operation start point.

SUMMARY OF THE INVENTION

An electric bending endoscope apparatus includes an electric bending endoscope, a bending control device, an image processing device, and a display device. The electric bending endoscope includes a bending wire having a bending portion at an inserting portion and a plurality of members for bending the bending portion, a bending motor which drives the bending wire, an electromagnetic clutch which reversibly switches a status for transmitting driving force by transmitting the driving force of the bending motor to the bending wire and a status for disconnecting the driving force, a potentiometer which detects an operating status of the bending wire and detects the bending status of the bending portion, a track ball for instructing a bending operation by outputting a bending instructing signal which relatively changes a bending direction and the amount of bending of the bending portion, a mark portion for detecting whether or not the bending portion is in at least one predetermined bending status, and an electromagnetic brake which detects the mark portion and sends to an operator a notification indicating that the bending portion is in the predetermined bending portion. The bending control device controls the bending direction and the amount of bending of the bending portion based on the bending instructing signal outputted from the track ball in the electric bending endoscope. The image processing device generates a video signal of an observing image captured by the electric bending endoscope. The display device displays the video signal generated by the image processing device as an endoscope image.

The above and other objects, features and advantages of the invention will become more clearly understood from the following description referring to the accompanying drawings.

BRIEF DESCRIPTION OF THE DRAWINGS

FIGS. 1 to 4B are diagrams for explaining a first embodiment;

FIG. 1 is a diagram for explaining one construction of an electric bending endoscope apparatus;

FIG. 2 is a flowchart for explaining a bending operation of the electric bending endoscope;

FIG. 3 is a diagram for explaining the operation of the electric bending endoscope apparatus;

FIG. 4B is a diagram for explaining a joystick having a stick portion as another example of the bending instructing signal input means;

FIGS. 5 and 6 are diagrams for explaining a second embodiment;

FIG. 5 is a diagram showing another structure of an electric bending endoscope apparatus;

FIG. 6 is a diagram for illustrating the operation of the electric bending endoscope apparatus;

FIGS. 7A to 14 are diagrams for explaining a third embodiment;

FIG. 7A is a diagram for illustrating one observing status when a bending portion is bent at an angle of 90° or more;

FIG. 9 is a diagram for explaining the structure of the electric bending endoscope apparatus;

FIG. 10 is a flowchart for explaining a freely bending operation;

FIG. 11 is a diagram for illustrating a bending status of the bending portion when an endoscope is inserted in the large intestine;

FIG. 12 is a diagram for illustrating bending angle regulating means which prevents the bending at an angle over 90° in the freely bending status;

FIG. 13A is a diagram for explaining the bending angle regulating means which bends the bending portion only in the single direction to reduce the bending angle in the freely bending status;

FIG. 13B is a diagram for illustrating the operation of the bending angle regulating means; and FIG. 14 is a diagram for explaining the construction and the operation of the bending angle regulating means which bends the bending portion in the single direction to reduce the bending angle in the freely bending status.

DETAILED DESCRIPTION OF THE PREFERRED EMBODIMENTS

Hereinbelow, embodiments of the present invention will be described with reference to the drawings.

A first embodiment of the present invention will be described with reference to FIGS. 1 to 4B.

Figure 1:
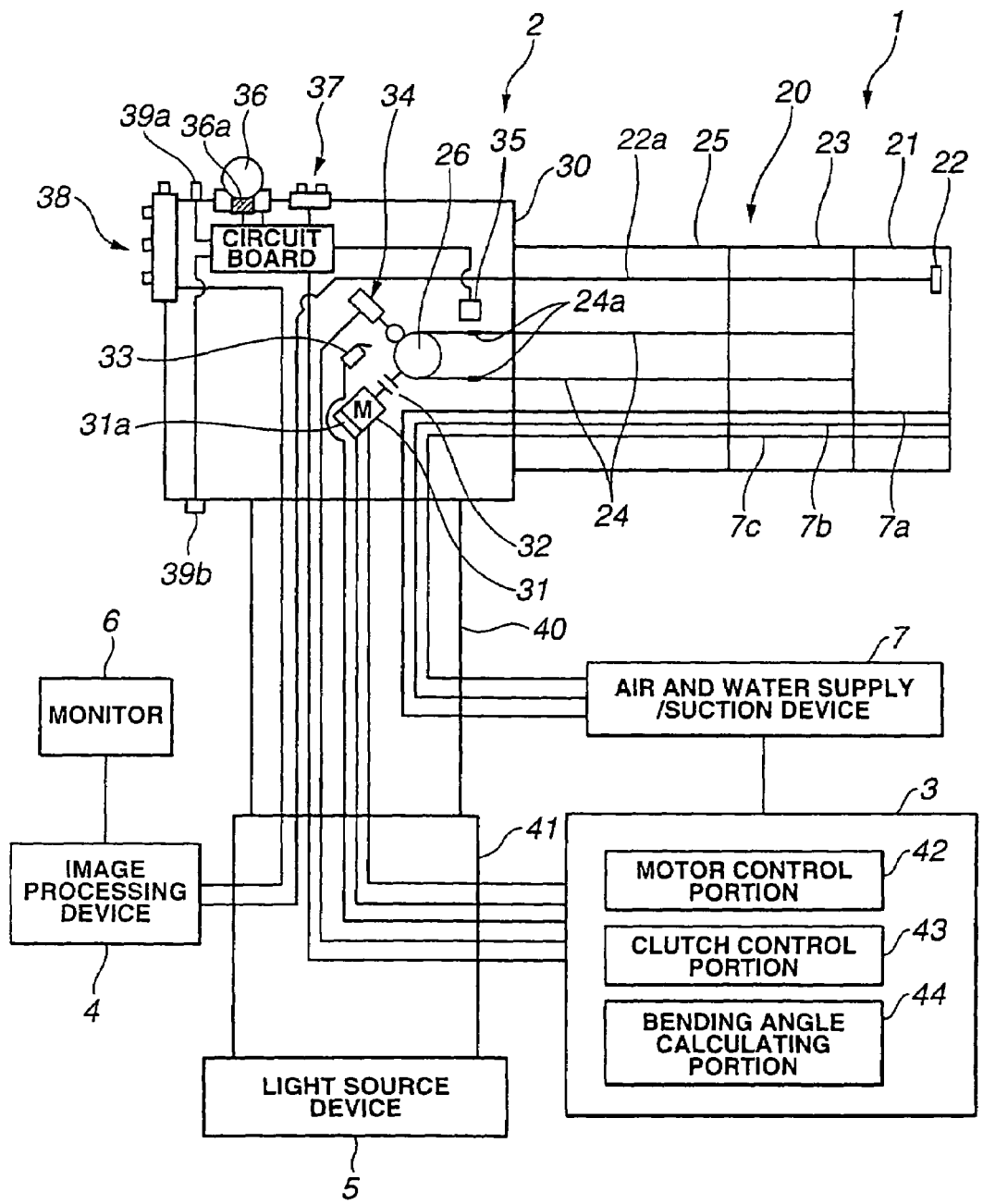

Referring to FIG. 1, an electric bending endoscope apparatus 1 according to the first embodiment comprises an electric bending endoscope (hereinafter, referred to as an endoscope) 2, a bending control device 3, an image processing device 4, a light source device 5, and a monitor 6 as a display device.

The endoscope 2 has an endoscope inserting portion (hereinafter, referred to as an inserting portion) 20. A distal end hard portion 21 is arranged to a distal end portion of the inserting portion 20. A bending portion 23 is consecutively installed to the distal end hard portion 21. The distal end hard portion 21 incorporates, e.g., an image pick-up device 22. The bending portion 23 is bent by electrically stretching bending wires 24 forming bending driving means.

The bending control device 3 has a motor driving signal generating portion (hereinafter, abbreviated to a motor control portion) 42 which generates a motor driving signal of a bending motor 31 as bending motive means for stretching the bending wires 24. The image processing device 4 converts and generates into a video signal, an image signal transmitted via a signal cable 22a extending from the image pick-up device 22. The light source device 5 supplies illumination light to an illumination optical system (not shown) of the endoscope via a light guide fiber bundle (not shown). An endoscope image is displayed on the monitor 6 by outputting the video signal generated by the image processing device 4.

The inserting portion 20 includes, e.g., an airline 7a, a waterline 7b, and a suction line 7c. The airline 7a, the waterline 7b, and the suction line 7c are connected to an air and water supply/suction device 7. The bending control device 3 and the image processing device 4 are electrically connected via a signal line (not shown).

The endoscope 2 comprises an elongated inserting portion 20, an operating portion 30 commonly functioning as a grip portion, and a universal cord 40 extending from a side portion of the operating portion 30. A connector portion 41 connected to the light source device 5 is arranged at the base end portion of the universal cord 40.

The inserting portion 20 comprises the distal end hard portion 21, the bending portion 23, and a flexible-tube portion 25. The image pick-up device 22 such as a CCD, as an observation optical system, is arranged to the distal end hard portion 21. The bending portion 23 is consecutively installed to the distal end hard portion 21, and a plurality of bending pieces are jointed and are formed to freely be bent vertically and horizontally. The flexible-tube portion 25 is elongated and soft and is consecutively installed to the bending portion 23.

The inserting portion 20 includes the vertical bending wires 24 and horizontal bending wires (not shown), which bend the bending portion 23, extending from the operating portion 30.

Hereinbelow, a description is given of the structure of the vertical bending wire 24. Further, the structure of the horizontal bending wires with the same structure as that of the vertical bending wires 24 is neither shown nor mentioned for the sake of a brief description.

Both end portions of the bending wires 24 are connected and fixed to a chain (not shown). The chain meshes with a rotatable vertical sprocket 26 forming the bending driving means. Thus, the bending wires 24 fixed to the chain are stretched by rotating the sprocket 26 in a predetermined direction. Then, the bending portion 23 is bent in a direction corresponding to the stretch of the bending wires 24.

The sprocket 26 is arranged, for example, in the operating portion 30. In the sprocket 26, driving force of the vertical bending motor 31 of a DC motor as a rotating driving source is transmitted via an electromagnetic clutch 32 as the means for restoring transmission and disconnection of the driving force.

The electromagnetic clutch 32 can reversibly, namely, physically detach the bending motor 31 and the sprocket 26. A status detecting switch 33 as means for detecting a transmitting and disconnecting status always detects whether the electromagnetic clutch 32 is in a status for transmitting the driving force or in a status for disconnecting the driving force.

The amount of rotation of the sprocket 26 rotated by the bending motor 31 is detected by a potentiometer 34 as means for detecting a bending status.

Further, the bending wires 24 have mark portions 24a forming means for detecting a predetermined bending status which are arranged in a line at predetermined positions when the bending portion 23 is in a non-bending status and vertical and horizontal optical sensors 35 forming the means for detecting the predetermined bending status which detect that the mark portions 24a are arranged in a line at the predetermined positions. Reference numeral 31a denotes an encoder which detects the rotation of the bending motor 31.

The operating portion 30 comprises a track ball 36, an air and water supply/suction switch 37, various scope switches 38, a clutch operating switch 39a, etc. The track ball 36 has an electromagnetic brake 36a as means for notifying a predetermined bending status. The air and water supply/suction switch 37 instructs an air supply status, a water supply status, or a suction status. The various scope switches 38 control the image processing device 4 such as a freeze operation of the endoscope image displayed on the screen of the monitor 6. The clutch operating switch 39a switches the electromagnetic clutch 32 to the status for transmitting the driving force or the status for disconnecting the driving force.

The track ball 36 is means for inputting a bending instructing signal of means for instructing a bending operation which instructs the bending direction, the amount of bending, and the bending speed of the bending portion 23. The track ball 36 instructs the change in relational position to the bending portion 23 by the rotation. A rotating direction of the track ball 36 corresponds to a bending direction of the bending portion 23. The number of revolution or the amount of rotation of the track ball 36 corresponds to a time for driving the motor at a constant speed, that is, the amount of bending of the bending portion 23.

The electromagnetic brake 36a always applies predetermined energizing force to the track ball 36. Thus, the track ball 36 rotates by a predetermined amount of force.

The electromagnetic brake 36a is switched on/off based on a detecting signal outputted from the optical sensor 35. In other words, the optical sensor 35 detects that the mark portions 24a are aligned at the predetermined positions and then the detecting signal is outputted to a substrate from the optical sensor 35. Then, the energizing force of the electromagnetic brake 36a is reset at the moment. Thus, rotating resistance of the track ball 36 is reduced at the moment. That is, when the bending status of the bending portion 23 changes to the non-bending status, the track ball 36 smoothly rotates as compared with a normally operating status and it is notified to an operator that the bending portion 23 enters the non-bending status.

The electromagnetic clutch 32 is switched to the status for disconnecting the driving force by operating the clutch operating switch 39a, thereby causing the bending portion 23 having the bending wire 24 which is not tensed. This status indicates a freely bending status in which external force freely changes the bending status of the bending portion 23.

The electromagnetic clutch 32 is restored from the status for disconnecting the driving force to the status for transmitting the driving force by operating the clutch operating switch 39a, thereby becoming an angle operating status in which the bending portion 23 is bent by the track ball 36.

The bending control device 3 includes a motor control portion 42, a clutch control portion 43, and a bending angle calculating portion 44 as means for detecting the bending status. When an electric signal is received from the track ball 36, the motor control portion 42 determines whether the bending motor 31 is the vertical one or the horizontal one and controls the rotating direction and the amount of rotation. The clutch control portion 43 receives an instructing signal from the clutch operating switch 39a and switches the electromagnetic clutch 32 to the status for transmitting the driving force or the status for disconnecting the driving force. The bending angle calculating portion 44 calculates the bending direction and the bending angle of the bending portion 23 based on an output signal which is outputted from the potentiometer 34.

The bending control device 3 receives status information notifying that the bending motor 31 is abnormally operated. The status information received by the bending control device 3 enables a screen 6a of the monitor 6 to display a warning by the switching to flicker display.

Reference numeral 39b denotes a switch for abnormal time as means for forcedly disconnecting the driving force which forcedly switches the status for transmitting the driving force to the status for disconnecting the driving force. Upon emergency, the switch 39b for abnormal time is operated together with the clutch operating switch 39a, thus, stops the supply of power to the connecting portion of the electromagnetically connected bending wires 24, resets the connecting status, and irreversibly disconnects the bending wires 24. According to the first embodiment, an outer surface of the switch 39b for abnormal time is colored as red.

A description is given of a relationship between the rotating operation of the track ball 36 and the change in bending status of the bending portion 23 with reference to a flowchart of FIG. 2.

In step S1, the track ball 36 is rotated in a desired direction by a desired amount for the bending operation. Consequently, an electric signal corresponding to the rotating direction and the amount of rotation of the track ball 36 is outputted to the motor control portion 42.

The motor control portion 42 receives the electric signal corresponding to the rotating direction and the amount of rotation of the track ball 36 and, in step S2, it selects the corresponding bending motor 31 based on the inputted electric signal. After that, the motor control portion 42 generates a driving signal for driving the bending motor 31 in a direction corresponding to the bending instructing signal and outputs the driving signal to the corresponding bending motor 31.

Then, in step S3, the predetermined bending motor 31 starts to rotate in a predetermined direction. Consequently, the bending wire 24 is stretched or contracted and the bending portion 23 starts to bend in step S4.

In step S5, after the bending motor 31 drives for a predetermined time, the bending operation of the bending portion 23 stops. Then, the track ball 36 stops the rotation and enters a re-operation waiting status.

In step S6, it is determined whether or not the endoscope image displayed on the screen of the monitor 6 indicates a target portion. Here, when the desired endoscope image is displayed on the screen of the monitor 6, the image is observed by holding the track ball 36. On the other hand, when the endoscope image displayed on the screen of the monitor 6 is different from the desired image, the processing routine returns to step S1 whereupon the track ball 36 is re-operated in the desired direction.

As mentioned above, the track ball 36 stops to rotate and then enters the re-operation waiting status. A stop position becomes a start position upon re-operation. In other words, the stop position corresponds to the start position upon bending the bending portion again. Therefore, when the track ball 36 rotates after stopping the bending operation, the bending status of the bending portion 23 in the stop status changes from the stop position by the amount of rotation and the rotating direction of the track ball 36.

When the electromagnetic clutch 32 is in the status for transmitting the driving force, as long as the operator continuously operates the track ball 36, a relationship between the bending instruction via the track ball 36 and the bending status of the bending portion 23 keeps unique.

On the contrary, when the clutch operating switch 39a is operated and the bending portion 23 enters the freely bending status by setting the electromagnetic clutch 32 to the status for disconnecting the driving force, the inserting portion 20 can be inserted along the luminal wall. The inserting portion 20 is inserted into the luminal wall, then, external force upon the inserting operation changes the bending status of the bending portion 23. The bending status of the bending portion 23 in this case is different from that when the bending portion 23 is in the freely bending status by operating the clutch operating switch 39a. Consequently, the operator determines the change in bending status based on the endoscope image displayed on the screen of the monitor 6, and memorizes the bending status of the bending portion 23 as an image. However, since the inserting portion 20 is twisted or advanced and returned and thus the endoscope image changes, the operator cannot perform the above operation.

When the clutch operating switch 39a is operated and the bending portion 23 is switched to the angle operating status from the freely bending status, the operator starts again to rotate the track ball 36 based on the memorized image. Then, the bending status of the bending portion 23 changes and the endoscope image displayed on the monitor 6 also changes.

When the bending status of the bending portion 23 imaged by the operator matches the actual bending status of the bending portion 23, an operator's desired image is obtained. For example, a dark portion 104 shown in FIG. 8B is displayed nearly at the predetermined position of the monitor 6.

On the other hand, when the bending status imaged by the operator is different from the actual bending status, the desired dark portion 104 is not displayed on the monitor 6. As a result, the operator cannot recognize the bending portion.

However, according to the first embodiment, the optical sensor 35 determines whether or not the bending portion 23 is in the non-bending status depending on whether or not the mark portions 24a are aligned at the predetermined position. The optical sensor 35 detects based on the alignment of the mark portions 24a that the bending portion 23 is in the non-bending status and, then, the energizing status using the electromagnetic brake 36a is reset and the amount of rotation of the track ball 36 is reduced. Accordingly, the operator can operate the track ball 36 by grasping that the bending portion 23 is in the non-bending status.

Incidentally, the means for detecting the bending status is not limited to the potentiometer 34, and can be a tension sensor which detects the bending angle by detecting the tension of the bending wire 24 or equipment which detects the bending angle by combining the potentiometer and the tension sensor.

A description is given of the operation of the electric bending endoscope apparatus 1 with the above-mentioned structure.

Referring to FIG. 3, in step S8, the electric bending endoscope apparatus 1 is configured by connecting the devices 3, 4, 5, 6, and 7 to the electric bending endoscope 2 which is subjected to sterilization process and which has the bending portion 23 in the freely bending status. Then, the power is turned on. In step S9, the bending portion 23 changes to the angle operating status from the freely bending status by setting the electromagnetic clutch 32 to the status for transmitting the driving force in conjunction with the power-on.

In step S10, the operator grips the operating portion 30 and the inserting portion 20 by both the hands so as to insert the inserting portion 20 in the celom. In this case, the track ball 36 is rotated, thereby bending the bending portion 23 in a desired direction. In step S11 the optical sensor 35 detects whether or not the bending portion 23 is in the non-bending status during the inserting operation.

In step S12, the optical sensor 35 detects that the mark portions 24a are aligned at the predetermined position. Then, the optical sensor 35 outputs a detecting signal and reduces the amount of rotation of the track ball 36. Accordingly, the operator can recognize that the bending portion 23 is in the non-bending status during the observation.

When the inserting portion is desired to be inserted in the freely bending status, for example, during the inserting operation, the electromagnetic clutch 32 is switched to the status for disconnecting the driving force by operating the clutch operating switch 39a. Then, in step S13 the bending portion 23 enters the freely bending status from the angle operating status, and the processing routine advances to step S14.

The bending portion 23 is in the freely bending status, thereby freely changing the bending status of the bending portion 23 under the influence of the external force. In step S14, the optical sensor 35 detects whether or not the bending portion 23 is in the non-bending status.

In step S15, the optical sensor 35 detects that the mark portions 24a are aligned at the predetermined position and then outputs the detecting signal, thus to reduce the amount of rotation of the track ball 36. Consequently, during the observation in the freely bending status, the operator can recognize that the bending portion 23 is almost in the non-bending status by touching the track ball 36 by the finger.

In step S16, the inserting operation is executed continuously in the freely bending status while the clutch operating switch 39a is in the status for disconnecting the driving force. Alternatively, in step S17, the inserting operation is performed in the angle operating status while the clutch operating switch 39a is in the status for transmitting the driving force.

Incidentally, when the bending portion 23 is restored to the angle operating status, the rotating resistance of the track ball 36 is reduced when the bending portion 23 is almost in the non-bending status as shown in step S11 or S12.

In step S18, it is selected whether the examination is continued or the inserting portion 20 is removed. Upon continuing the examination, the processing routine advances to step S16. On the contrary, upon removing the inserting portion 20, the inserting portion 20 is removed and the power is thereafter turned off in step S19. Then, the electromagnetic clutch 32 is set to the status for disconnecting the driving force in conjunction with the power-off. Namely, after finishing the observation, the bending portion 23 enters the freely bending status by turning off the power.

As mentioned above, it is always observed whether or not the bending portion is bent by arranging the mark portions at the predetermined position of the bending wires and by installing the optical sensor for observing the arrangement position of the mark portions. When the optical sensor detects that the alignment of the mark portions indicates that the bending portion is in the non-bending status, the rotating resistance of the track ball is decreased thus to notify to the operator that the bending portion is in the non-bending status.

Hence, the operator can execute the inserting operation while recognizing that the bending portion changes from the bending status to the non-bending status during the observation. The operator can promptly bend the bending portion by the track ball without calibration when the bending portion changes to the angle operating status from the freely bending status because he performs the inserting operation based on the non-bending status irrespective of the freely bending status or the angle operating status.

The bending status of the bending portion is in the non-bending status according to the first embodiment. However, the bending status detected by the optical sensor is not limited to the non-bending status and the optical sensor may detect the bending status desired by the operator.

Further, the non-bending status is directly notified to the operator by increasing or decreasing the operating resistance of the track ball 36 according to the first embodiment. However, the non-bending status may be notified by vibrating the operating portion 30 or the bending status of the bending portion 23 may be notified to the operator by displaying e.g., a symbol on the screen of the monitor 6.

Figure 4A:
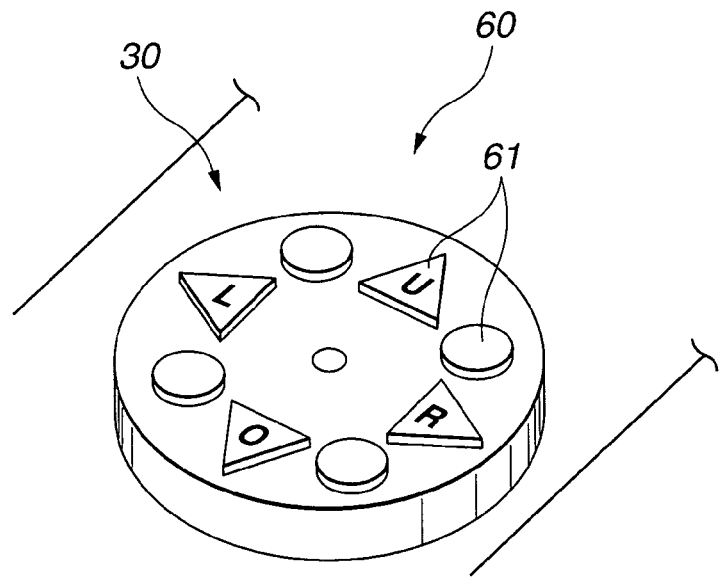
FIG. 4A is a diagram for explaining a pressure-sensitive pad as another example of bending instructing signal input means.

Furthermore, the means for inputting the bending instructing signal is the track ball 36 according to the first embodiment. However, the means for inputting the bending instructing signal is not limited to the track ball 36 and may be an operating switch which instructs the change in relative position of the amount of bending or the bending speed as well as the bending direction. Referring to FIG. 4A, the means for inputting the bending instructing signal may be an operating switch 60 having pressure-sensitive pads 61 arranged at eight positions corresponding to the bending directions, namely, containing vertical and horizontal positions and intermediate positions in the vertical and horizontal directions. Alternatively, referring to FIG. 4B, the means for inputting the bending instructing signal may be an operating switch 65 as a joystick which returns to an upstanding status by releasing the finger from a stick portion 66. In addition, although not shown, it may be a pointing device such as a pointer or a mouse.

In the operating switch 60 shown in FIG. 4A, the bending portion 23 is bent in the pressing direction by pressing the pressure-sensitive pad 61 corresponding to any direction. The bending motor 31 is driven to change the bending status during pressing the pressure-sensitive pads 61. The rotating time of the bending motor 31 which rotates at a constant speed may be set by the number of pressing times of the pressure-sensitive pads 61. Or, the rotating speed of the bending motor 31 may acceleratively be changed by changing the pressure of the pressure-sensitive pads 61.

Figure 4B:
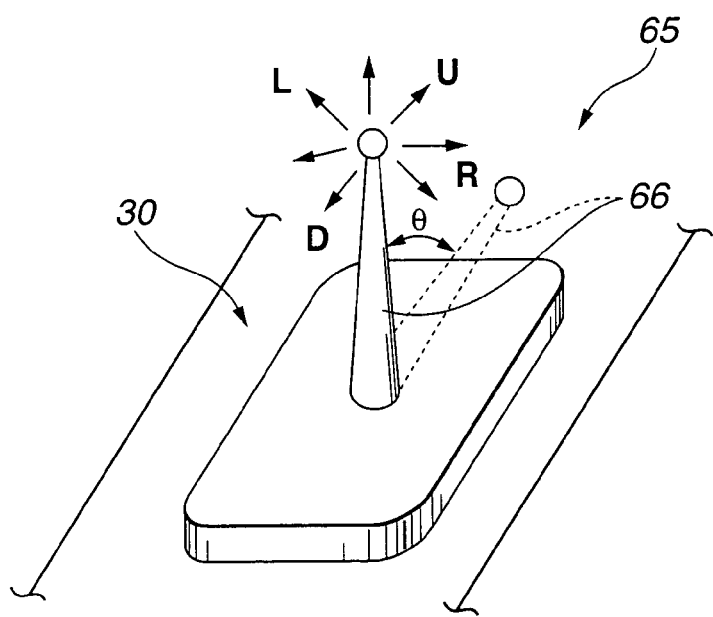

In the operating switch 65 shown in FIG. 4B, an inclining direction of the stick portion 66 indicates the bending direction of the bending portion 23. The bending motor 31 rotates at a constant speed to change the bending status during the inclining operation. The rotating time of the bending motor 31 which rotates at a constant speed may be set by the change of an inclining angle θ. Or, the rotating speed of the bending motor 31 may acceleratively be changed.

A second embodiment of the present invention will be described with reference to FIGS. 5 and 6.

According to the second embodiment, the bending status of the bending portion is notified to the operator by displaying, e.g., a symbol on the screen of the monitor.

Further, according to the second embodiment, in place of the arrangement of the mark portions 24a, the optical sensor 35, and the electromagnetic brake 36a, the bending control device 3 includes a storing portion 45, a comparing portion 46, and a bending status notifying portion 47. In addition, the image processing device 4 includes a notifying information display circuit 48.

Figure 5:
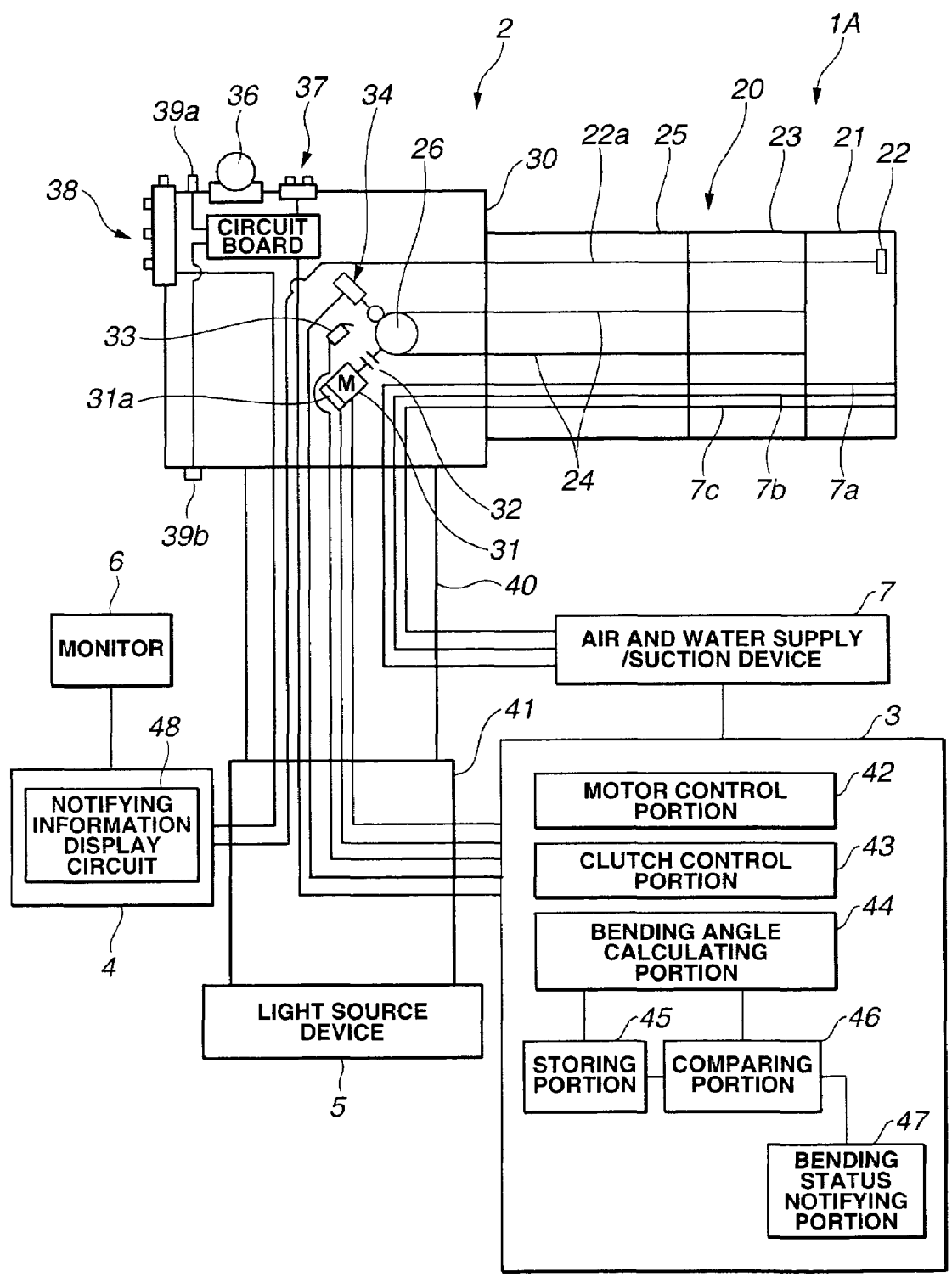

Referring to FIG. 5, in an electric bending endoscope apparatus 1A according to the second embodiment, the bending control device 3 comprises the motor control portion 42, the clutch control portion 43, the bending angle calculating portion 44, the storing portion 45, the status comparing portion (hereinafter, abbreviated to the comparing portion) 46, and the bending status notifying portion 47.

The storing portion 45 previously stores the non-bending status of the bending portion 23 as information on the bending status based on the calculation result of the bending angle calculating portion 44. The comparing portion 46 always compares and determines whether or not the bending status of the bending portion 23 is approximate to the information on the bending status stored in the storing portion 45 during the operation. The bending status notifying portion 47 is notifying means which sends to the operator the notification indicating that the bending status of the bending portion 23 is approximate to the information on the bending status stored in the storing portion 45 based on a comparison result of the comparison portion 46.

The image processing device 4 includes the notifying information display circuit 48. When the comparing portion 46 determines that the bending status is approximate to the information on the bending status, the notifying information display circuit 48 displays a predetermined symbol which notifies the operator of the non-bending status on the screen of the monitor 6 after receiving a notifying signal outputted from the bending status notifying portion 47.

Accordingly, according to the second embodiment, the comparing portion 46 always compares and determines whether or not the bending status of the bending portion 23 is approximate to the non-bending status corresponding to the information on the bending status stored in the storing portion 45. When the comparing portion 46 determines that the bending status is approximate to the information on the bending status, the notifying signal is outputted to, for example, the notifying information display circuit 48 arranged to the image processing device 4 so as to send the notification indicating the foregoing to the operator from the bending status notifying portion 47. Then, the screen of the monitor 6 displays a predetermined symbol which sends a notification indicating the non-bending status to the operator.

The comparing portion 46 compares and determines the information on the bending status by setting a play range of a predetermined angle. That is, when the bending status of the bending portion 23 matches the information on the bending status stored in the storing portion 45 or enters the play range of the angle, such a fact is sent to the operator.

Hence, when the bending status of the bending portion 23 is approximate to the non-bending status, the operator can recognize that the bending portion 23 is approximate to the non-bending status from the predetermined symbol displayed on the screen of the monitor 6.

Other structures are the same as those according to the first embodiment and the same reference numerals denote the same components and description thereof is omitted.

Herein, the operation of the electric bending endoscope apparatus 1A with the above-mentioned structure will be described.

Referring to FIG. 6, in step S21, the electric bending endoscope apparatus 1A is configured by connecting the devices 3, 4, 5, 6, and 7 to the electric bending endoscope 2 which is subjected to sterilization process and which has the bending portion 23 in the freely bending status. Then, the power is turned on. In step S22, the bending portion 23 changes to the angle operating status from the freely bending status by setting the electromagnetic clutch 32 to the status for transmitting the driving force in conjunction with the power-on.

In step S23, the operator grips the operating portion 30 and the inserting portion 20 by both the hands so as to insert the insertion portion 20 in the celom. In this case, the track ball 36 is appropriately rotated. Thus, the bending portion 23 bends in the desired direction. In step S24, the comparing portion 46 compares the bending status of the bending portion 23 with the information on the bending status stored in the storing portion 45 during the inserting operation. In step S25, when the bending status of the bending portion 23 is approximate to the non-bending status corresponding to the information on the bending status which is previously stored in the storing portion 45, a symbol designated by the operator is displayed on the screen of the monitor 6. Thus, during the observation, the operator can recognize that the bending portion 23 is almost in the non-bending status.

When the inserting portion is desired to be inserted in the freely bending status, for example, during the inserting operation, the electromagnetic clutch 32 is switched to the status for disconnecting the driving force by operating the clutch operating switch 39a. Then, in step S26, the bending portion 23 enters the freely bending status from the angle operating status, and the processing routine advances to step S27.

The bending portion 23 is set to the freely bending status, thereby freely changing the bending status of the bending portion 23 under the influence of the external force. In step S27, the comparing portion 46 compares the bending status of the bending portion 23 with the information on the bending status stored in the storing portion 45. In step S28, when the bending status of the bending portion 23 is approximate to the non-bending status corresponding to the information on the bending status which is previously stored in the storing portion 45, the symbol designated by the operator is displayed on the screen of the monitor 6. Thus, the operator can recognize that the bending portion 23 is almost in the non-bending status during the observation.

In step S29, the inserting operation is executed continuously in the freely bending status while the clutch operating switch 39a is in the status for disconnecting the driving force. Alternatively, in step S20, the inserting operation is performed in the angle operating status while the clutch operating switch 39a is in the status for transmitting the driving force.

Incidentally, when the bending portion 23 is restored to the angle operating status, the symbol designated by the operator is displayed on the screen of the monitor 6 when the bending portion 23 is almost in the non-bending status as shown in step S24 or S25.

In step S31, it is selected whether the examination is continuously performed or the inserting portion 20 is removed. Upon continuously executing the examination, the processing routine advances to step S29. On the contrary, upon removing the inserting portion 20, the inserting portion 20 is removed and the power is thereafter turned off in step S32. Then, the electromagnetic clutch 32 is set to the status for disconnecting the driving force in conjunction with the power-off. Namely, after finishing the observation, the bending portion 23 enters the freely bending status by turning off the power.

As mentioned above, the storing portion previously stores the non-bending status of the bending portion. Simultaneously with the starting operation of the observation, the comparing portion compares the bending status of the bending portion with the information on the bending status stored in the storing portion. When the bending status of the bending portion is approximate to the information on the bending status stored in the storing portion, the symbol designated by the operator is displayed on the screen of the monitor to send the notification indicating such a fact. Accordingly, during the observation, the operator can recognize that the bending status of the bending portion is in the non-bending status.

Other operations and advantages are the same as those according to the first embodiment.

The non-bending status is stored as the information on the bending status in the storing portion 45 according to the second embodiment. However, the information on the bending status stored in the storing portion 45 is not limited to the non-bending status and the bending status desired by the operator may be stored in the storing portion 45 as the information on the bending status.

The information on the bending status stored in the storing portion 45 is not limited to the single piece of information. In addition to the non-bending status, horizontally and vertically bending statuses at an angle of 60° may be stored as the information on the bending status. In this case, the symbol displayed on the screen changes depending on the difference of the bending status of the bending portion 23.

Further, it is notified to the operator that the bending status of the bending portion 23 is approximate to the information on the bending status by displaying the symbol on the screen of the monitor 6. However, it may be notified to the operator not only by displaying the symbol on the screen but also by outputting the notifying signal from the bending status notifying portion 47, e.g., by reducing the bending speed of the bending portion 23 so as to slowly change the endoscope image on the screen.

A third embodiment of the present invention will be described with reference to FIGS. 7A to 14.

When the bending portion 23 of the electric bending endoscope 2 is in the freely bending status, external force from the luminal wall acts to the bending portion 23, thus to modify the bending portion 23 by a large amount of bending in an unexpected direction.

Figure 7A:
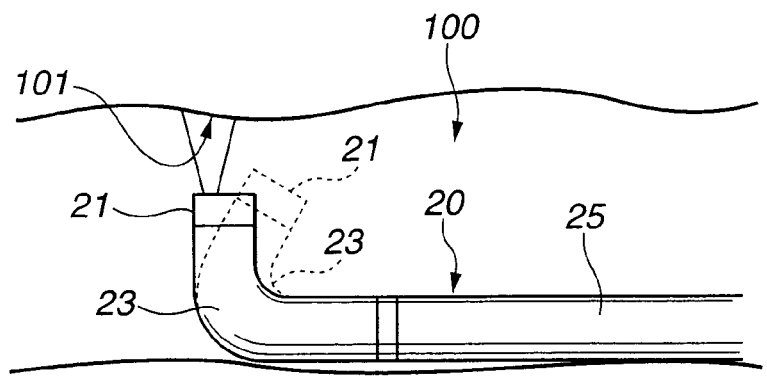
Figure 7B:
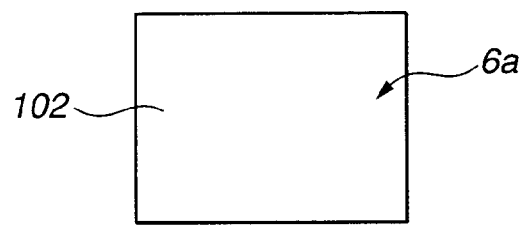
FIG. 7B is a diagram showing an endoscope image in the one observing status shown in FIG. 7A.

In this case, when the bending portion 23 is bent and modified in a luminal portion 100 at an angle of 90° or more as shown by a broken line 7A, an image 102 of a luminal wall 101 without an index is displayed with a uniform brightness on the overall screen 6a of the monitor 6 as shown in FIG. 7B. Upon displaying the image 102, there is the danger that the operator loses his sense of direction. According to the third embodiment, the operator cannot determine the direction for rotating the track ball 36 because of the use of the track ball 36 which instructs the bending direction and the bending amount as the means for instructing the bending operation. Thus, a default might be caused in the operation of the endoscope.

Figure 8A:
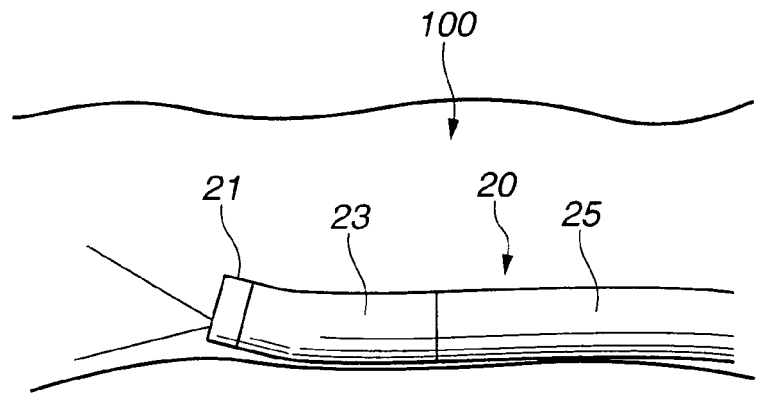
FIG. 8A is a diagram for illustrating another observing status when the bending portion is bent at an angle of 90° or less.
Figure 8B:
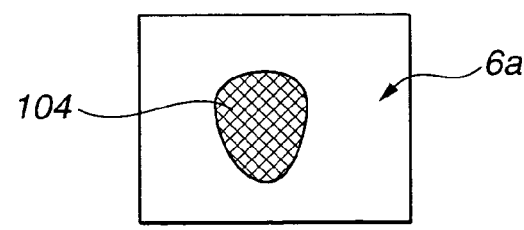
FIG. 8B is a diagram showing an endoscope image in the observing status shown in FIG. 8A.

On the contrary, when the luminal portion is observed in the facing direction or in the almost-facing direction as shown in FIG. 8A in the bending status of the bending portion 23 at an angle of 90° or less as shown by a solid line in FIG. 7A, the operation for slightly rotating the track ball 36 causes a dark portion 104 to be displayed on the screen 6a of the monitor 6 as means for detecting the luminal center in which illumination light showing a deep portion in the luminal portion 100 does not reach as shown in FIG. 8B.

That is, the operation for displaying the dark portion 104 on the screen 6a enables the operator to easily recognize the positional relationship without losing his sense of direction and to rotate the track ball 36. The operation of the endoscope stably continues.

Figure 9:
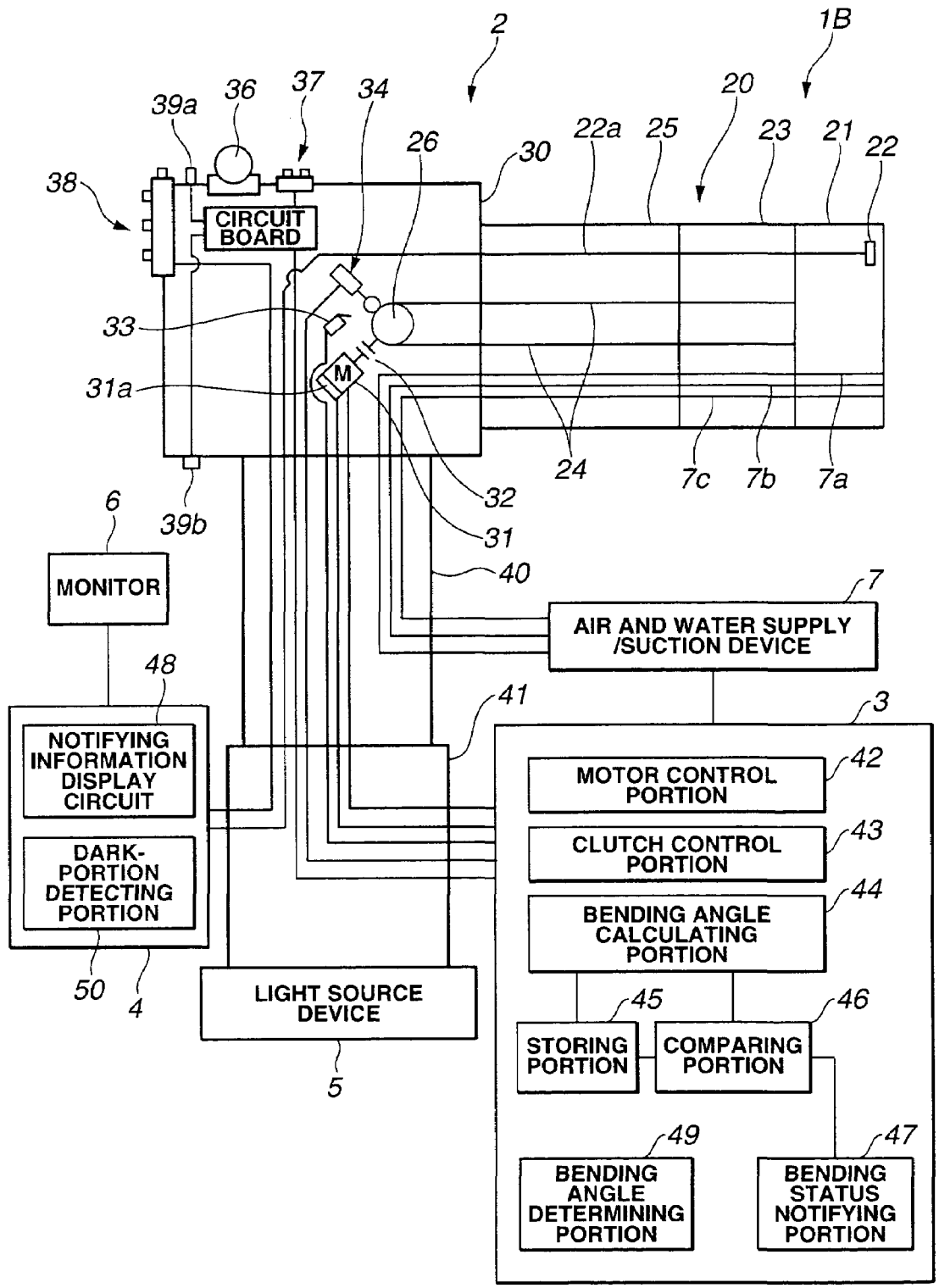
Figure 10:
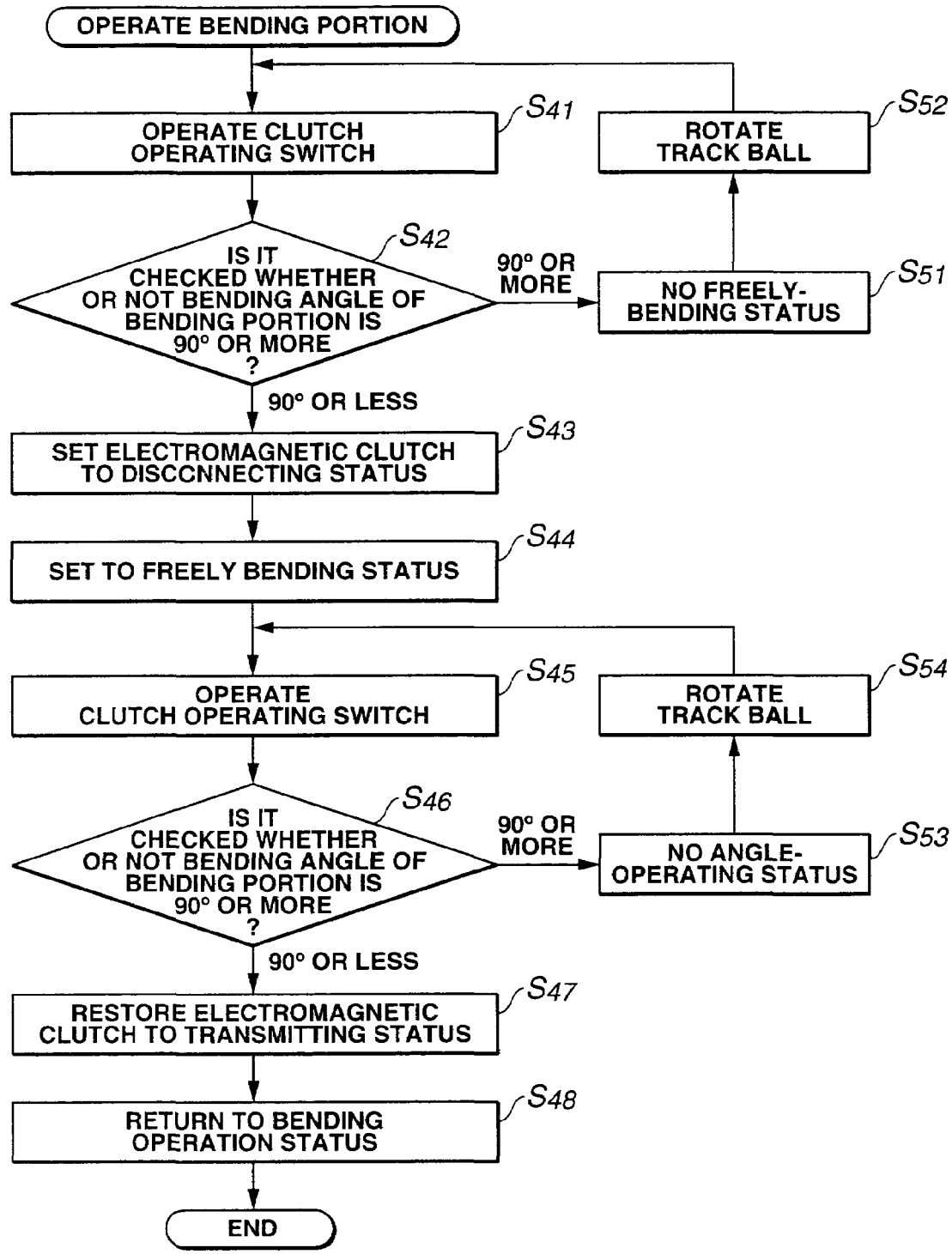

According to the third embodiment, referring to FIG. 9, the bending control device 3 in an electric bending endoscope apparatus 1B includes a bending angle determining portion 49 which determines the bending angle of the bending portion 23 calculated by the bending angle calculating portion 44 is 90° or more.

When the bending angle determining portion 49 determines that the bending angle of the bending portion 23 is 90° or more, the electromagnetic clutch 32 does not change from the status for transmitting the driving force to the status for disconnecting the driving force in view of the operability of the endoscope 2 upon operating the clutch operating switch 39a. Alternatively, the electromagnetic clutch 32 does not change from the status for disconnecting the driving force to the status for transmitting the driving force, namely, the operating status of the electromagnetic clutch 32 does not change.

The image processing device 4 may include a dark-portion detecting portion 50. In other words, the dark-portion detecting portion 50 detects whether or not the screen 6a of the monitor 6 displays the dark portion 104. Only when the screen 6a displays the dark portion 104, the electromagnetic clutch 32 may change to the status for disconnecting the driving force or the status for transmitting the driving force upon operating the clutch operating switch 39a.

A description is given of the operation of the electric bending endoscope apparatus 1B with the above-mentioned structure.

First, the operator grips the operating portion 30 and the inserting portion 20 by both the hands so as to insert the inserting portion 20 in the luminal portion. In this case, the track ball 36 is appropriately rotated, thereby bending the bending portion 23. Alternatively, the bending portion 23 is set to the freely bending status and the inserting portion 20 is inserted into a target portion. When the operator wants the freely bending status, he operates the clutch operating switch 39a in step S41.

Then, the clutch operating switch 39a outputs an instructing signal to the bending control device 3 and the processing routine advances to step S42. In step S42, the bending angle determining portion 49 in the bending control device 3 determines whether or not the bending angle of the bending portion 23 is 90° or more.

Herein, when the bending angle determining portion 49 determines that the bending angle of the bending portion 23 is 90° or less, the processing routine advances to step S43. The driving operation of the bending motor 31 stops and the clutch control portion 43 outputs the instructing signal in accordance with the instructing signal outputted from the clutch operating switch 39a. Then, the electromagnetic clutch 32 changes to the status for disconnecting the driving force.

The bending status detecting switch 33 inputs to the bending control device 3 a notifying signal indicating that the electromagnetic clutch 32 is in the status for disconnecting the driving force. Then, in step S44, the bending portion 23 is in the freely bending status.

In step S45, the clutch operating switch 39a re-outputs the instructing signal to the bending control device 3 by re-operating the clutch operating switch 39a so as to bend the bending portion 23. Then, in step S46, the bending angle determining portion 49 in the bending control device 3 determines whether or not the bending angle of the bending portion 23 is 90° or more.

When the bending angle determining portion 49 determines that the bending angle is 90° or less, the processing routine advances to step S47. In step S47, the clutch control portion 43 outputs the instructing signal to the electromagnetic clutch 32 in accordance with an instructing signal outputted from the clutch operating switch 39a. Since the bending control device 3 receives the notifying signal indicating that the electromagnetic clutch 32 is in the status for disconnecting the driving force, the electromagnetic clutch 32 is restored into the status for the transmitting driving force.

Thus, in step S48, the track ball 36 returns to the status in which the bending portion 23 is bent. The luminal wall is observed by appropriately bending the bending portion 23.

Through proper operations in steps S41 to S48, the inserting portion 20 is removed from the luminal portion after completing the observation. The bending portion 23 is set to the freely bending status and the examination using the endoscope ends.

When the bending angle determining portion 49 determines in step S42 that the bending angle of the bending portion 23 is 90° or more, in step S51, it is notified to the operator that the bending angle of the bending portion 23 is 90° or more by displaying a message indicating no freely-bending status on the screen of the monitor. Upon the notification, in step S52, the operator adjusts the bending angle so that it is 90° or less by properly operating the track ball 36 and, then, the processing routine shifts to step S41 again.

When the bending angle determining portion 49 determines in step S46 that the bending angle of the bending portion 23 is 90° or more, in step S53, it is notified to the operator by displaying a message indicating no angle-operating status on the screen of the monitor. In this case, in step S54, the bending angle is adjusted so that it is 90° or less by properly operating the track ball 36 and, then, the processing routine shifts to step S45 again.

As mentioned above, when it is determined whether or not the bending angle of the bending portion is 90° or more and it is thus determined that the bending angle is 90° or less, the operating instruction is received from the clutch operating switch and the electromagnetic clutch can be detached. Consequently, the operator can preferably operate the endoscope without losing his sense of direction.

Figure 11:
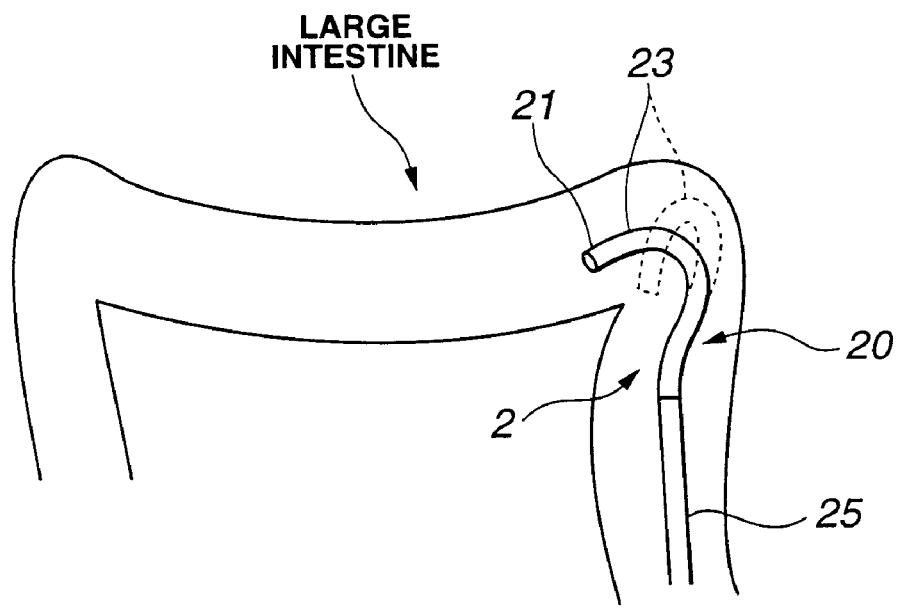

Referring to FIG. 11, in an endoscope for under-digestive organ of the lower position, when the distal end hard portion 21 of the endoscope 2 inserted in the large intestine is near the non-bending portion, the dark portion might be displayed on the screen of the monitor upon bending the bending portion 23 at the angle of 90° or more as shown by a broken line.

Referring to FIG. 8B, in the endoscope for under-digestive organ of the lower position, even when the screen 6a displays the dark portion 104, the operation for switching the electromagnetic clutch 32 to the status for disconnecting the driving force or the status for transmitting the driving force is prevented upon operating the clutch operating switch 39a by structuring a control program for according the bending angle priority over the operation for displaying the dark portion image for the sake of safety.

Figure 12:
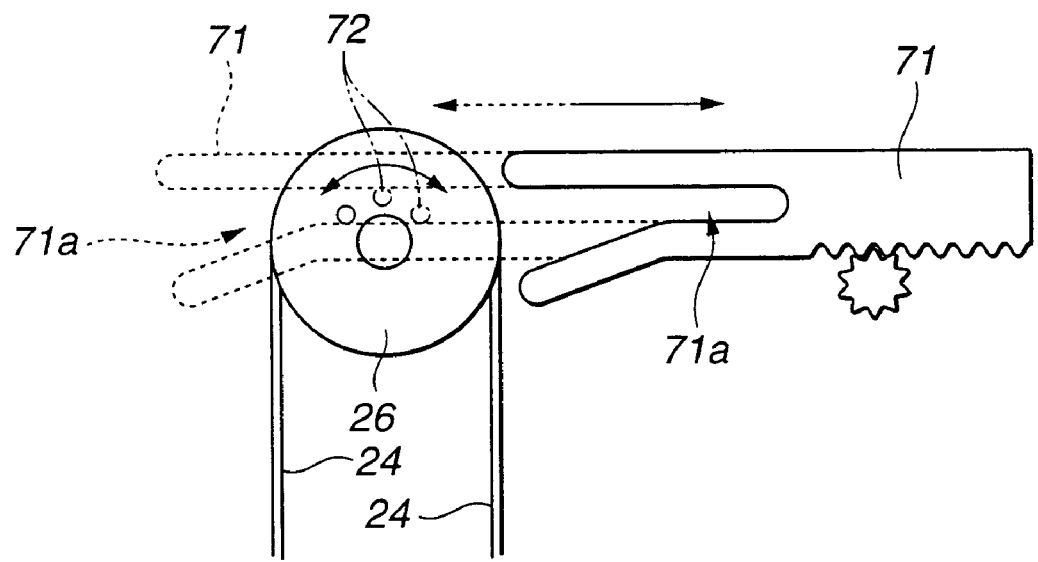

Further, according to the third embodiment, referring to FIG. 12, when the bending portion 23 in which the electromagnetic clutch 32 is in the status for disconnecting the driving force is in the freely bending status, means for regulating the bending angle is arranged to prevent the operation for bending the bending portion 23 at an angle of more than 90°.

The means for regulating the bending angle comprises a slidable regulating portion main body 71 forming a regulating groove 71a shown by a solid line and a broken line and a regulating pin 72 which is projected at a predetermined position of the sprocket 26. When the electromagnetic clutch 32 is in the status for transmitting the driving force, the regulating portion main body 71 is arranged at a position shown by a solid line.

When the status detecting switch 33 detects that the electromagnetic clutch 32 is in the status for disconnecting the driving force, the regulating portion main body 71 is slidden and arranged to a position shown by a broken line, and the regulating pin 72 is moved only in the regulating groove 71a. Thus, it is certainly prevented that the bending portion 23 is bent at an angle of more than 90° in both directions.

Figure 14:
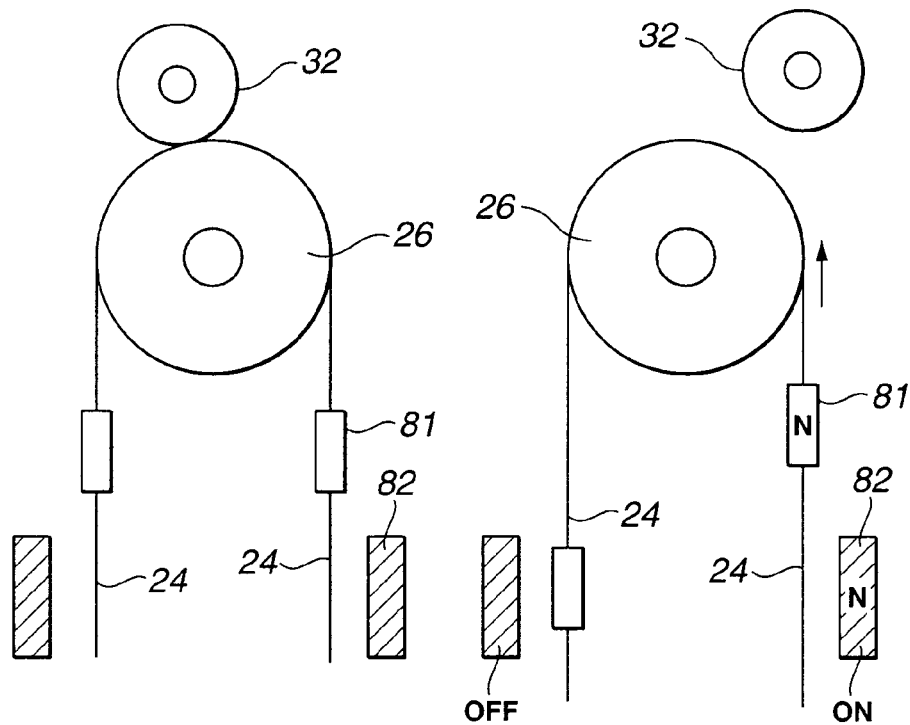

Further, according to the third embodiment, when the electromagnetic clutch 32 is in the status for disconnecting the driving force and is thus in the freely bending status, means for regulating the bending direction is arranged to bend the bending portion 23 only in the single direction to reduce the bending angle thereof as shown in FIGS. 13A to 14.

Referring to FIG. 13A, the means for regulating the bending direction comprises a permanent magnet 81 fixed to the bending wire 24 and an electromagnet 82 which controls the on/off operation that the bending direction is regulated to bend the bending portion 23 in the direction of the bending angle of 0°.

Referring to FIG. 13B, when the status detecting switch 33 detects that the electromagnetic switch 32 is in the status for disconnecting the driving force, the control operation is set to the on-operation so that the electromagnet 82 corresponding to the bending direction reacts to the permanent magnet 81.

Thus, it is prevented without fail that the bending angle of the bending portion 23 is further increased.

Referring to FIG. 14, the means for regulating the bending direction comprises a clasp portion 85 which is arranged to the bending wire 24 projecting to the single direction and a pair of ratchet portions 88 including an actuator 87 having a notch portion 86 in which the clasp portion 85 is engaged, for sliding and moving the bending portion so that the bending angle is 0°.

The status detecting switch 33 detects that the electromagnetic clutch 32 is in the status for disconnecting the driving force and, then, the actuator 87 corresponding to the bending direction is moved to enter a waiting status for engaging the clasp portion 85 in the notch portion 86.

Accordingly, the increase in bending angle of the bending portion is prevented without fail.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending endoscope apparatus comprising:
   an endoscope having an insertion portion which is inserted into a subject in order to observe the inner portion of the subject, the insertion portion having a bending portion which can be bent in a desired direction at the distal end side thereof;
   a bending direction instructing device for outputting an instruction signal for bending the bending portion in the desired direction;
   a bending motive device for generating a drive force for bending the bending portion in response to the instruction from the bending direction instructing device;
   a bending driving device for bending the bending portion based on the drive force generated by the bending motive device;
   a first bending status detecting means for detecting the operating status in a moving range of the bending driving device which is moving based on the drive force in accordance with the instruction of the bending direction instructing device;
   a second bending status detecting means arranged in the moving range of the bending driving device for detecting only that the bending portion is in a predetermined bending status by detecting that the bending driving device is at a predetermined position, the second bending status detecting means not using a detection result of the first bending status detecting means; and
   a bending status notifying means for notifying an operator that the bending portion bends in a predetermined direction or angle based only on a detecting result of the second bending status detecting means.

2. An electric bending endoscope apparatus according to claim 1, wherein the second bending status detecting means comprises an optical sensor which detects a mark portion arranged on the bending operation device.

3. An electric bending endoscope apparatus according to claim 1, wherein the bending direction instructing device comprises an operation device which is operated by the operator.

4. An electric bending endoscope apparatus according to claim 3, wherein the bending status notifying means is an electromagnetic brake for providing a predetermined operation resistance to the operation device.

5. An electric bending endoscope apparatus according to claim 1, wherein the bending status notifying means comprises a display device for displaying that the bending portion is in coincidence with the predetermined bending status.

6. An electric bending endoscope apparatus according to claim 1, wherein the bending status notifying means notifies the operator by using vibration that the bending portion is in coincidence with the predetermined bending status.

7. An electric bending endoscope apparatus according to claim 1, further comprising:
   a bending angle judging portion for judging a bending angle based on the detecting result of the first bending status detecting means.

8. An electric bending endoscope apparatus according to claim 1, further comprising:
   a) an image pick-up device provided at the distal end of the insertion portion;
   b) an image processing device for producing a video signal based on an image signal outputted from the image pickup device; and
   c) a display device for displaying the video signal produced by the image processing device as an endoscope image.

9. An electric bending endoscope apparatus according to claim 1 further comprising:
   a bending control device for controlling the bending motive device based on an instruction signal outputted from the bending direction instructing device and the detecting result of the first bending status detecting means.

10. An electric bending endoscope apparatus according to claim 1 further comprising:
   a clutch provided between the driving device and the bending operation device for switching between a transmission status and a disconnection status of a driving force to the bending operation device.

11. An electric bending endoscope apparatus according to claim 10, further comprising:
   a bending regulating device for regulating the bending of the bending portion when the clutch is in the disconnection status.

12. An electric bending endoscope apparatus according to claim 11, wherein the bending regulating device regulates at least one of a bending direction and a bending amount of the bending portion when the clutch is in the disconnection status.

13. An electric bending endoscope apparatus according to claim 10, wherein the clutch is an electromagnetic clutch for switching from the disconnection status to the transmission status be receiving electric power supply.

14. An electric bending endoscope apparatus according to claim 13, further comprising:
   a switching means for forcedly switching the electromagnetic clutch from the transmission status to the disconnection status.

15. An electric bending endoscope apparatus according to claim 14, wherein the switching means is a supply stopping means for forcedly stopping the electric power supply to the electromagnetic clutch.

16. An electric bending endoscope apparatus according to claim 10, further comprising:
   a detection switch for detecting whether the clutch is in the transmission status or in the disconnection status of the driving force.

17. An electric bending endoscope apparatus according to claim 10, further comprising a bending angle judging portion for determining the bending angle of the bending portion based on a detection result of the first bending status detecting means.
   wherein the clutch can switch between the transmission status and the disconnection status of the driving force to the bending operation device when the judging result of the bending angle judging portion indicates a predetermined angle or less.

18. An electric bending endoscope apparatus according to claim 10, further comprising:
   a dark portion detecting part for detecting a dark portion of a lumen displayed on the display device.

19. An electric bending endoscope apparatus according to claim 18, wherein the clutch switches between the transmission status and the disconnection status of the driving force to the bending operation device based on the detecting result of the dark portion detecting part.

* * * * *